United States Patent [19]
Stark

[11] Patent Number: 6,124,134
[45] Date of Patent: Sep. 26, 2000

[54] GLUCOSE RELATED MEASUREMENT METHOD AND APPARATUS

[76] Inventor: Edward W. Stark, 160 W. End Ave., Suite 3M, New York, N.Y. 10023

[21] Appl. No.: 08/697,433

[22] Filed: Aug. 23, 1996

Related U.S. Application Data

[63] Continuation of application No. 08/515,286, Aug. 15, 1995, abandoned, which is a continuation of application No. 08/083,056, Jun. 25, 1993, abandoned.

[51] Int. Cl.[7] ............................ G01N 21/31; G01N 21/25; G01N 33/00
[52] U.S. Cl. .................... 436/63; 356/329; 250/339.02; 250/339.05; 250/339.06; 250/339.07; 250/339.09; 250/339.12; 250/341.5; 422/82.05; 422/82.09; 436/66; 436/67; 436/95
[58] Field of Search .................. 250/339.01, 339.02, 250/339.05, 339.06, 339.07, 339.09, 339.12, 341.1, 341.5; 356/329; 422/68.1, 82.05, 82.09; 436/63, 67, 95, 66; 702/85

[56] References Cited

U.S. PATENT DOCUMENTS

| | | | |
|---|---|---|---|
| 3,581,199 | 5/1971 | Spitz | 324/77 |
| 4,255,659 | 3/1981 | Kaufman et al. | 250/370.09 |
| 4,357,673 | 11/1982 | Willis et al. | 364/582 |
| 4,407,290 | 10/1983 | Wilber | 128/633 |
| 4,427,889 | 1/1984 | Müller | 128/633 X |
| 4,781,195 | 11/1988 | Martin | 128/633 |
| 4,784,486 | 11/1988 | Van Wagenen et al. | 356/301 |
| 4,805,623 | 2/1989 | Jöbsis | 128/633 |
| 4,882,492 | 11/1989 | Schlager | 128/633 X |
| 4,997,281 | 3/1991 | Stark | 356/328 |
| 5,068,536 | 11/1991 | Rosenthal | 128/633 X |
| 5,204,532 | 4/1993 | Rosenthal | 250/341 |
| 5,379,238 | 1/1995 | Stark | 364/578 |
| 5,433,197 | 7/1995 | Stark | 128/633 |
| 5,568,400 | 10/1996 | Stark et al. | 364/498 |

FOREIGN PATENT DOCUMENTS 222419  5/1987  European Pat. Off. .

OTHER PUBLICATIONS

S. Scopatz et al, *Proc. SPIE—Int. Soc. Opt. Eng.* 1989, 1055, 306–313.
S. B Kenney et al. *Proc. SPIE—Int. Soc. Opt. Eng.* 1991, 1480, 82–93.
T.G.R. Rawlins et al. *Phys. Med. Biol.* 1981, 26, 425–434.
S.R. Hawkins et al. *Proc. SPIE—Int. Soc. Opt. Eng.* 1983, 366, 41–49.

(List continued on next page.)

*Primary Examiner*—Arlen Soderquist
*Attorney, Agent, or Firm*—Schwegman, Lundberg, Woessner & Kluth PA

[57] ABSTRACT

A method of and apparatus for determining stable and labile glycated compound levels in blood. Electromagnetic energy covering a multiplicity of wavelength bands within a wavelength range from 380 nm to 2500 nm is directed into a sample volume containing blood. Portions of the energy representative of both the source energy and energy after interacting with material within the sample volume are collected. The energy portions carry information relating to the source energy and the levels of labile and stable compounds within the sample volume, respectively. The portions are converted into electrical signals representative of the intensities of the respective portions in each of the multiplicity of wavelength bands. The electrical signals are pretreated in accordance with known information to remove deviations from established reference conditions to form data signals that are a function of the fractional portion of the energy in each of the wavelength bands absorbed and scattered by the material in the measurement volume. Selected groups of the data signals are processed in accordance with chemometric models developed from analysis of such data signals together with known values of the analytes derived from measurements on a calibration set of samples larger in number than the number of wavelength bands included in the set of the selected groups of data signals to develop analyte signals representative of the amounts of glycated compounds for which chemometric models have been developed and utilized. The analyte signals may be stored and displayed in a form suitable for medical use.

13 Claims, 7 Drawing Sheets

OTHER PUBLICATIONS

P.S.C. VanDer Plas et al. *Spectrochim. Acta* 1987, 42B, 1027–1038.
R.L. Streit *J. Acoust. Soc. Am.* 1989, 86, 1827–1834.
H. Koshiishi *Shashin Sokuryo to Rimoto Senshingu* 1992 31, 22–30.
K.V. Dang et al. *Proc. SPIE—Int. Soc. Opt. Eng.* 1992, 1686, 125–135.
J. Krolik et al. *J. Acoust. Soc. Am.* 1992, 92, 238–243.
W. Büchtemann *IEEE Trans. Electron Devices* 1980, ED-27, 189–193.
R.D. Nelson et al. *J. Appl. Phys.* 1982, 53, 4262–4269.
G.R. Sims et al. *Opt Eng.* 1987, 26, 999–1007.
D.S. Smith et al. *Proc. SPIE—Int. Soc. Opt. Eng.* 1988, 972, 2–8.
W.S. Lee et al. *Electron. Lett.* 1988, 24, 1143–1145.
B. Touzet et al. *Proc. SPIE—Int. Soc. Opt. Eng.* 1989, 1013, 146–153.
V.I. Blynskii et al *Phys. Status. Solidi A* 1990, 121, 227–233.
R.D. Piccard et al. *Rev. Sci. Instrum.* 1991, 62, 584–594.
G.P. Ellis *J. Chem. Soc.* (*B*) 1966, 572–576.
Y.M. Shilov et al. *Chem. Abstr.* 1975, 82, 77138b.
F.S. Parker "Applications of Infrared Spectroscopy in Biochemistry, Biology and Medicine" Plenum Press: New York, 1971, 100–141.
V.M. Tul'chinskii et al. *Chem. Abstr.* 1977, 86, 106970g.
M. Trovati et al. *Acta Diabet. Lat.* 1981, 18, 207–211.
Y. Ozaki et al. *Appl. Spectrosc.* 1989, 43, 723–725.
Osuoji, C.I. et al. *Biochem. Soc. Trans.* 1973, 1, 458–461.
Ng Kwai Hang, K.F. et al. *Can. J. Biochem.* 1980, 58, 319–324.
Trovati, M. et al. *Chem. Abstr.* 1982, 96, 16830P.
Trovati, M. et al. *Chem. Abstr.* 1982, 96, 158417h.
Cecchini, G. et al. *Chem. Abstr.* 1987, 106, 30865k.
Heise, H. M et al. *Mikrochim. Acta* 1990, 3, 79–85.
Keiehnau, J. *Chem. Abstr.* 1991, 114, 59688f.
Martens, H. et al. *Anal. Appl. Spectrosc. 2* 1991, 221–239.
Martens, H. et al. *J. Pharm. Biomed. Anal.* 1991, 9, 625–635.
H. Zeller et al. *Int. J. Artif. Org.* 1989, 12, 129–135.
H.M. Heise et al. *Anal. Chem.* 1989, 61, 2009–2015.
G. Janatsch et al. *Anal. Chem.* 1989, 61, 2016–2023.
H.M. Heise et al. *Chem. Abstr.* 1991, 114, 20445z.
H. Martens et al. *Chem. Abstr.* 1991, 115, 247131p.
H. Martens et al. *Chem. Abstr.* 1992, 116, 120150j.
K.J. Ward et al. *Appl. Spectrosc.* 1992, 46 959–965.
M.R. Robinson et al. *Clin Chem.* 1992, 38 1698–1622.
J.W. Hall et al. *Clin. Chem.* 1992, 38, 1623–1631.
D.M. Haaland et al. *Appl. Spectrosc.* 1992, 46, 1575–1578.
R. Marbach et al. *Appl. Spectrosc.* 1993, 47, 875–881.
P. Bhandare et al. *Appl. Spectrosc.* 1993, 47, 1214–1221.
L.A. Marquardt et al. *Anal. Chem.* 1993, 65, 3271–3278.
G.W. Small et al. *Anal. Chem.* 1993, 65, 3279–3289.

GLUCOSE RELATED MEASUREMENT METHOD AND APPARATUS

This is a continuation of application Ser. No. 08/515,286, filed Aug. 15, 1995, now abandoned which is a continuation of application Ser. No. 08/083,056, filed Jun. 25, 1993, now abandoned.

BACKGROUND OF THE INVENTION

I. Field of the Invention

The present invention relates to the in-vivo and in-vitro measurement of glucose-related analytes by spectroscopic means.

II. Description of the Prior Art

Diabetes is a metabolic disorder caused by a body's failure to either produce insulin or use insulin effectively. The hormone, insulin, enables a body to utilize glucose. Approximately 1.4 million Americans suffer from Type I diabetes, where the body fails to produce insulin, and an additional 13 million Americans suffer from type II diabetes, where the body fails to utilize insulin effectively. Currently, seven percent of Americans have diabetes. This percentage is expected to rise to approximately ten percent by the year 2000.

Recent studies have indicated that frequent monitoring and control of blood glucose levels reduces the possibility of serious complications in diabetics by fifty to sixty percent. These studies utilized measurements of the stable glycated hemoglobin complex $HbA_{1c}$ to evaluate the long-term time average blood glucose level over a several month period immediately preceding the time the sample was taken. The long-term average is based on the approximately 120 day life of the red blood cells containing the glycated hemoglobin. $HbA_{1c}$ consists of 50 to 90% hemoglobin glycated by a ketoamine linkage at the beta chain N-terminal valine residue. Medical practitioners also use the level of the stable glycated albumin complex fructosamine within the blood serum to provide an evaluation of the approximately 2 to 3 week medium-term time average glucose level of the patient. These two measurements, combined with the immediate blood glucose level, are of great value in diagnosing and treating diabetes. There is medical evidence that the formation of glucose-protein and glucose-lipid complexes may be the direct cause of some of the degenerative effects of diabetes as well as those of aging. In addition to the stable complexes, glucose forms labile complexes with proteins and lipids which are the precursors of the stable complexes. The level of these labile complexes are in equilibrium with the glucose level of the surrounding medium and are therefore highly correlated with the present level of blood glucose. This is particularly true in-vivo because the equilibrium has not been disturbed by the collection or handling of an in-vitro sample. Pre-Hemoglobin $A_{1c}$ is a labile form of glycated Hb containing glucose bound in aldimine linkage to the beta chain N-terminal valine residue.

The methods currently used to directly measure the levels of stable glycated protein and lipid complexes are invasive in that they require the collection and preparation of a sample for analysis by one of several methods. For example, analysis of the sample may be performed using affinity chromatography, high performance liquid chromatography, ion-exchange chromatography, immunoassay, or calorimetry with thiobarbituric acid (TBA) for total glycated Hb or nitroblue tetrazolium (NBT) for glycated serum albumin. The various methods measure different fractions of the glycated proteins and lipids, some are relatively specific while others measure the total level of several types combined. In addition, they are typically time consuming and labor intensive. Recently, an immunoassay method and bench-top instrumentation for determination of $HBA_{1c}$ in the physician's office has been introduced (DCA 2000 Hemoglobin $A_{1c}$ System, Miles, Diagnostics Div.) that improves the speed and ease of analysis although it still requires a blood sample.

In-vitro measurement of the labile fraction of glycated protein and lipids is less common due to the difficulty of maintaining the labile fraction through chemical analysis procedures. In addition, direct in-vitro measurement of blood glucose is well established technology which largely obviates the medical need for in-vitro determination of labile glycated protein and lipid fractions. European Patent Application No. 86200311.8, having publication No. 0 222 419 A2, discloses non-invasive measurement of labile glycosylated hemoglobin in the blood using energy having a visible wavelength range between 520 and 620 nm in order to determine glycemia of a patient. This spectrophotometric method utilizes the shift in wavelength of an absorption peak determined by the ratio of absorption in two semi-areas of the visible spectrum divided at approximately 575 nm. The accuracy and precision of this method is limited by the high absorption of light in this region, which results in a low signal level, and the presence of spectral interferences from other substances present in the blood which cannot be resolved using only two spectral measurements.

One of the invasive methods of directly measuring blood glucose levels requires analysis of a blood sample taken from a patient. The blood sample may be obtained by pricking the patient's finger. The sample is analyzed using chemically treated strips which indicate by color the glucose level in the sample being tested. The strips may be visually compared to color standards or preferably placed in a reader which measures the color reaction on the strip and displays the glucose level. Other enzymatic assays utilize electrochemical or colorimetric measurement techniques. Because these techniques all require at least a finger prick to obtain a blood sample, they are suitable for neither the continuous monitoring nor the repeated testing at frequent intervals which is desirable for the tight control of blood glucose in diabetic patients that has been shown to reduce the long-term medical problems caused by diabetes.

Non-invasive methods and apparatus for direct determination of blood glucose utilizing spectroscopic measurements in the visible (380 to 780 nm) and near-infrared (780 to 2500 nm) regions of the electromagnetic spectrum are disclosed in U.S. Pat. Nos. 4,655,255, 4,882,492, 4,975,581, 5,068,536, 5,077,476, 5,086,229, 5,204,532 and others. To date, none of these direct, in-vivo determinations of blood glucose have reached the accuracy and reliability required for medical use in the management of diabetes. The spectral information utilized by these methods includes not only that generated by glucose in the blood but also that from glucose in the interstitial fluid and other tissues. The spectral information also contains interfering spectral information from the other constituents within the measurement volume.

U.S. Pat. No. 4,975,581, issued to Robinson, et al., discloses a method of and apparatus for determining the similarity of a biological analyte from a model constructed from known biological fluids utilizing a stored model and "an algorithm including (a) all independent sources of said intensity variations v. said wavelengths information from both said set of samples and said biological fluid and (b) more wavelengths than samples . . . "

Pulse oximetry is a related technology which utilizes near-infrared spectroscopy. Two wavelengths in the 700 to 900 nm region of the near-infrared spectrum are used to measure the oxygen saturation of the blood based on the spectral absorption difference between oxy- and deoxy-hemoglobin. The technique utilizes the temporal change in the oxy- and deoxy- hemoglobin absorption measurements caused by the pulsation of the blood pressure to remove steady-state interferences to these measurements.

OBJECTS AND SUMMARY OF THE INVENTION

Applicants invention is based on the recognition and discovery that a measurement of the labile glycated hemoglobin can be correlated to the present levels of glucose in the blood. Applicant's invention is also based on the recognition that a measurement of the total stable glycated hemoglobin or portions thereof, such as the $HbA_{1c}$ fraction, provides an index of the long-term time average of blood glucose levels. The normal level of glycated Hb is approximately 6% of the total Hb. This level increases to as much as 12 to 14% when the long-term average blood glucose is elevated. Applicant's invention is also based on the recognition that a measurement of the stable glycated serum protein or portions thereof, such as glycated albumin, similarly provides an index of the medium-term time average of blood glucose levels.

The measurements discussed above can be achieved by spectroscopic methods using electromagnetic energy in the visible (380 to 780 nm) and/or near-infrared (780 to 2500 nm) wavelength ranges. The absorption of visible and near-infrared light by the hemoglobin and serum proteins is modified when these molecules are glycated due to the influence of the attached glucose on both the electronic transitions and molecular vibrations which form the basis of the absorption of light by the molecule. Either non-invasive, in-vivo or invasive, in-vitro measurements can be made by these methods and both approaches to sampling have medical utility. Independent measurements are made of the light intensity in many relatively narrow wavelength bands within selected spectral regions using a source of light, means causing said light to interact with the blood and other components within a measurement volume, means for converting the intensities of light entering and leaving the measurement volume into electrical signals representing the effect of all the optical absorption and scattering losses resulting from the interaction of the light with the material within said measurement volume.

Data pretreatment modifies said signals by mathematical operations based on a priori knowledge to accomplish at least one of the following: (a) to remove known instrumental variations affecting the measurement to make the chemometric model independent of the particular instrument used to make the measurement, (b) to linearize the relationship between the measured spectral data and the value of the analyte, (c) to correct the baseline offset and multiplicative effect of scattering within the measurement volume and, (d) in the case of in-vivo, non-invasive measurements, to extract the pulse waveform relating to the blood component of the signal and to utilize this waveform to separate and filter the absorption signals arising from within the blood from those derived elsewhere in the measurement volume.

By special processing of the measured spectral data utilizing chemometric modeling techniques, several analyte values can be determined simultaneously. For example, $HbA_{1c}$, fructosamine, and pre-$HbA_{1c}$, can all be determined from a single measured spectrum using separate chemometric models for each analyte. To optimize the accuracy and precision of each of these models, the signals utilized are selected from the total set of wavelength bands, said selection being optimized for each analyte. Also, each model is derived from a calibration set of spectral measurements for which the associated analyte values are known by independent measurement using known analytical reference methods. In order to most accurately and precisely model the wide variety of compositions possible in biological systems, the number of independent calibration spectra and associated analyte values used is larger than the number of spectral bands included in the model.

The present, medium-term average, and long-term average blood glucose values can be computed based on their correlation to the labile and stable glycated hemoglobin and serum protein measurements.

The computed analyte values are stored to maintain a record and to allow recall and display to the user. In addition, a data link is provided to transmit the analyte values to a remote computer, to a data station, or to the controller of an insulin pump.

It is accordingly an object of the present invention to provide a method of and apparatus for non-invasively measuring labile glycated hemoglobin.

It is another object of the present invention to provide a method of and apparatus for non-invasively measuring stable glycated hemoglobin in the blood.

It is another object of the present invention to provide a method of and apparatus for non-invasively measuring stable glycated serum proteins in the blood.

It is another object of the present invention to provide a method of and apparatus for non-invasively measuring other labile and stable glycated proteins and lipids in the blood.

It is another object of the present invention to provide a method of and apparatus for measuring labile glycated hemoglobin in vitro within an invasively obtained blood sample.

It is another object of the present invention to provide a method of and apparatus for measuring stable glycated hemoglobin in vitro within an invasively obtained blood sample.

It is another object of the present invention to provide a method of and apparatus for measuring stable glycated serum proteins in vitro within an invasively obtained blood sample.

It is another object of the present invention to provide a method of and apparatus for measuring other glycated protein and lipid levels in vitro within an invasively obtained blood sample.

It is a further object of the present invention to accomplish the method and apparatus of the present invention by applying, visible light energy, or near-infrared energy or both to the sample.

It is still a further object of the present invention to process the measurement signals of labile glycated hemoglobin, stable glycated hemoglobin, and stable glycated serum protein using advanced signal processing techniques to achieve an accurate resultant signal representing present, long-term time average, and medium-term time average blood glucose levels respectively.

It is also an object of the present invention to provide a method of and apparatus for non-invasively determining blood glucose level using electromagnetic energy having wavelengths in the visible and near-infrared spectral ranges.

It is a further object of the present invention to provide a method of and apparatus for non-invasively determining blood glucose level using near-infrared wavelengths between 1110 and 1560 nanometers.

It is a further object of the present invention to provide a method of and apparatus for non-invasively determining blood glucose level using the temporal signal variations caused by the pulsatile flow of blood.

It is still another object of the present invention to store the analyte values determined, to display them on command, and to transmit them via an optical data link for the purpose of remote display or control of an insulin pump.

In accordance with the present invention, one method of determining the level of labile and stable glycated hemoglobin, glycated serum albumin, and other glycated protein and lipid fractions in blood comprises the steps of:
  a) supplying a source of electromagnetic energy covering a multiplicity of wavelength bands within the wavelength range from 380 to 2500 nm.;
  b) directing said source of energy into a sample volume containing blood comprising hemoglobin, glucose, albumin, and other components of the blood cells and plasma;
  c) collecting a first portion of said energy representative of said source energy;
  d) collecting a second portion of said energy after it has interacted with the material within the sample volume so as to carry information related to the amounts of glycated hemoglobin, glycated serum albumin, other glycated proteins and lipids, as well as other blood and tissue constituents present in the sample volume;
  e) converting said first and second portions of said energy into electrical signals representative of the intensities of said collected energy in each of said multiplicity of wavelength bands;
  f) pretreating said electrical signals in accordance with a priori known information to remove deviations from established reference conditions and combining said electrical signals to form data signals that are a function of the fractional portion of the energy in each of said wavelength bands absorbed and scattered by said material in said measurement volume;
  g) processing selected groups of said pretreated data signals in accordance with chemometric models developed from analysis of such pretreated data signals together with known values of the analytes derived from measurements on a calibration set of samples larger in number than the number of wavelength bands included in the set of said selected data signals to develop analyte signals representative of the amounts of those forms of glycated proteins and lipids for which chemometric models have been developed and utilized; and,
  h) storing and displaying said analyte signals in a form suitable for medical use.

In accordance with the present invention, a second method of determining the level of labile and stable glycated hemoglobin, glycated serum albumin, and other glycated protein and lipid fractions and blood glucose in blood non-invasively in-vivo comprises the steps above with the additional step of:
  extracting from the multiplicity of data signals a reference signal representative of the temporal waveform of the portion of the data signals derived from the blood within the sample volume and processing each of the multiplicity of data signals representing different wavelength bands in accordance with this reference waveform to derive blood data signals representative of the portion of the energy absorbed or scattered by the blood alone.

In accordance with the present invention, a third method provides analyte signals representative of one or more of the present, medium-term average, and long-term average levels of blood glucose based on the correlation of these values to the present values of labile glycated hemoglobin, stable glycated hemoglobin, and stable glycated albumin as determined in accordance with either of the methods above.

DETAILED DESCRIPTION OF THE INVENTION

Figure 1:
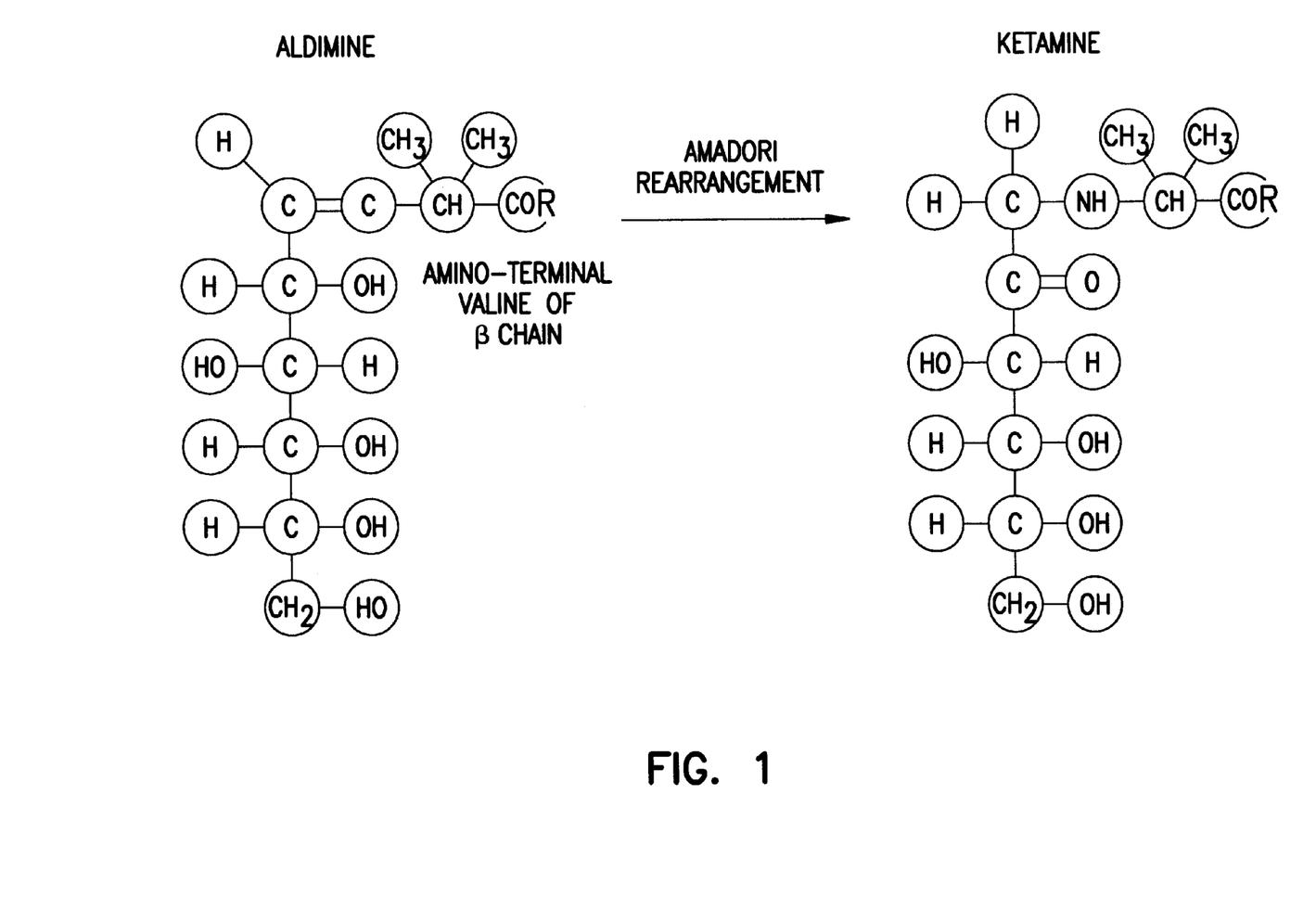
FIG. 1 is a chemical diagram of the aldimine and ketoamine adducts of hemoglobin and glucose.

Glucose molecules attach themselves to chemical compounds existing in the body. The chemical compounds include, but are not limited to hemoglobin, low density lipoprotein (LDL's) and serum proteins, e.g albumin. For example, when glucose is in the free aldehyde form, it can react with the hemoglobin molecule within the red cells of blood to form an aldimine adduct as shown in FIG. 1. Because this is a reversible reaction in equilibrium with the blood glucose, the aldimine adduct is labile. However, it can then undergo a shift in the double bond to carbon 2 in what is known as the "Amadori Rearrangement" to form a ketoamine adduct, also diagrammed in FIG. 1, which is a relatively irreversible arrangement of the hemoglobin and glucose molecules. This reaction can occur at a number of sites on the hemoglobin molecule such as the N-terminal valine and free amino groups of lysine. The changes in the chemical bonds, particularly the double bonds involving the first and second carbons of glucose, modify both the electronic transition and molecular vibration environments from those of free glucose and hemoglobin to those of the adducts. Therefore, the optical absorption spectra of free glucose and hemoglobin, the aldimine, and the ketoamine are each sufficiently different to form the basis for spectroscopic determination of the amounts of each form present in blood. $HbA_{1c}$ is the most prevalent of the ketoamine adducts with the β chain of hemoglobin, representing 5 to 6% of the total hemoglobin in persons without diabetes. The ketoamine adduct of glucose and albumin is the most prevalent among the serum proteins because albumin has the highest concentration of these proteins.

Because the formation of the ketoamine form of glycated hemoglobin and glycated albumin proceeds relatively slowly at a rate proportional to the glucose concentration and the lifetime of the hemoglobin and albumin molecules is limited, the amount of these adducts is related to the average glucose concentration over a period defined by the lifetime of the host molecule. Therefore, it is possible to utilize this correlation to determine the medium-term (2–3 weeks) and long-term average (up to 4 months) values of glucose in the blood from spectroscopic measurements of the ketoamine adducts of albumin and hemoglobin, respectively. Similarly, the correlation between the labile aldimine adducts, which can be measured spectroscopically, and the present value of free blood glucose can be used to determine blood glucose levels.

Figure 2:
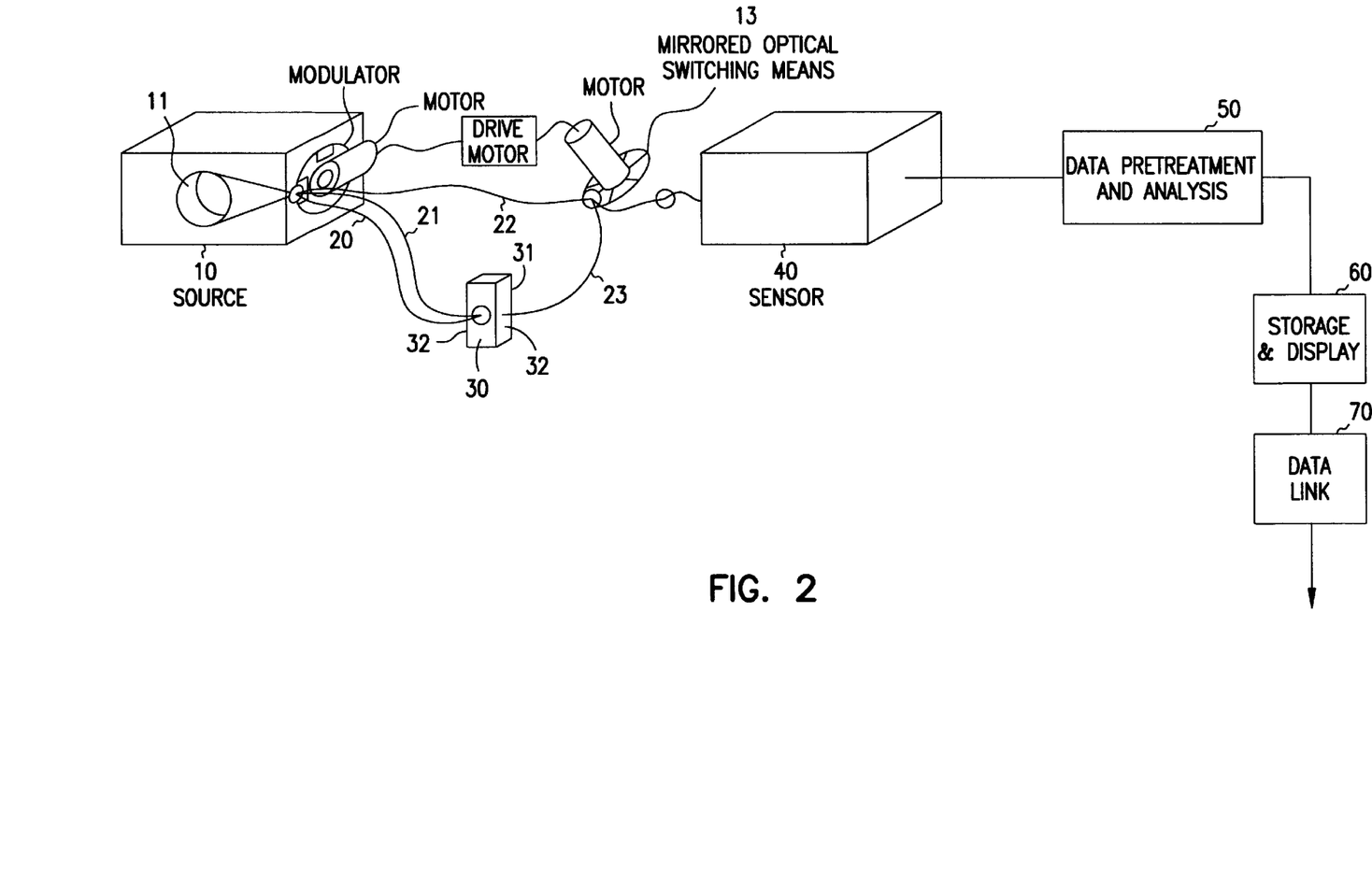
FIG. 2 is a schematic diagram of a first embodiment of the invention, particularly adapted for in-vitro measurement of glycated proteins and lipids by diffuse transmission.

Unlike the prior art which measures glycated proteins and lipids in-vitro by chemical reactions, chromatographic separation, or immunoassay involving reagents and sample manipulation, the present invention measures the level of glycated proteins and lipids based on the effects of glycation on the absorption of optical energy by the host molecule, e.g. hemoglobin and albumin. Therefore, sample preparation is not required and either in-vitro or in-vivo determination is possible. Reference is made to FIG. 2 of the drawing wherein a source 10 of optical energy is provided. In a first preferred implementation, source 10 comprises a tungsten-halogen lamp and reflector assembly 11. Source 10 illuminates a fiber-optic bundle assembly 20 with a wide range of wavelengths through an optical modulator 12 which in accordance with a defined multiplexing pattern directs the source energy to the sample channel 21, directs the source energy to a reference channel 22, and blocks the energy.

Fiber-optic bundle 20 is constructed so that the sample source channel 21 directs the source energy into the sample 30, which is contained in a cell 31 having transparent windows 32 on either side. In a preferred embodiment, the sample-source channel bundle 21 has a large cross sectional area and high numerical aperture so that the optical throughput is large, thus compensating for the scattering losses inherent to measurement of a blood sample containing cells. The reference channel 22 has a small cross sectional area because it conveys source energy directly to the sensor 40 with insignificant loss of optical throughput due to scattering. The areas are chosen to provide similar energy levels for the reference and sample signals. The energy diffusely transmitted through the sample 30 is collected by the sample-sensor fiber-optic channel 23 and transmitted to the sensor 40. Preferably, the cross-sectional area and numerical aperture of the sample-sensor fiber-optic channel 23 are matched to the optical throughput of sensor 40 and optical signal switching means 13 are provided to demultiplex the sample-reference information by switching the sensor input path between the channels. Alternatively, the optical throughput of the sensor may be shared between the sample-sensor channel and the reference channel by combining the respective fiber-optic bundles into a single bundle. This alternative is attractive when the required optical throughput for the reference channel is a small fraction of the sensor optical throughput.

Figure 3:
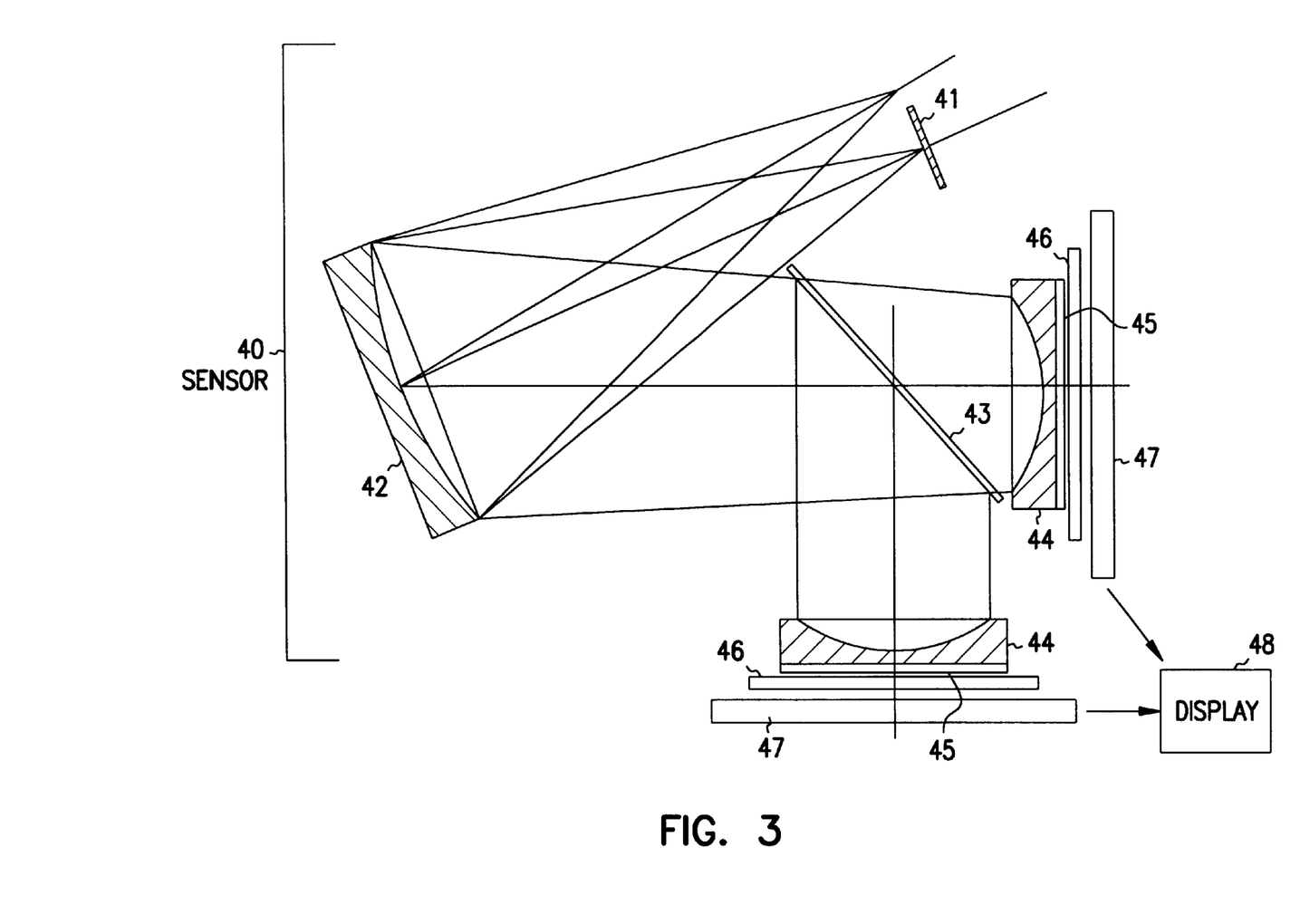
FIG. 3 is a schematic diagram of an improved diode-array grating spectrometer providing simultaneous measurement in the visible and near-infrared portions of the electromagnetic spectrum.
Figure 4:
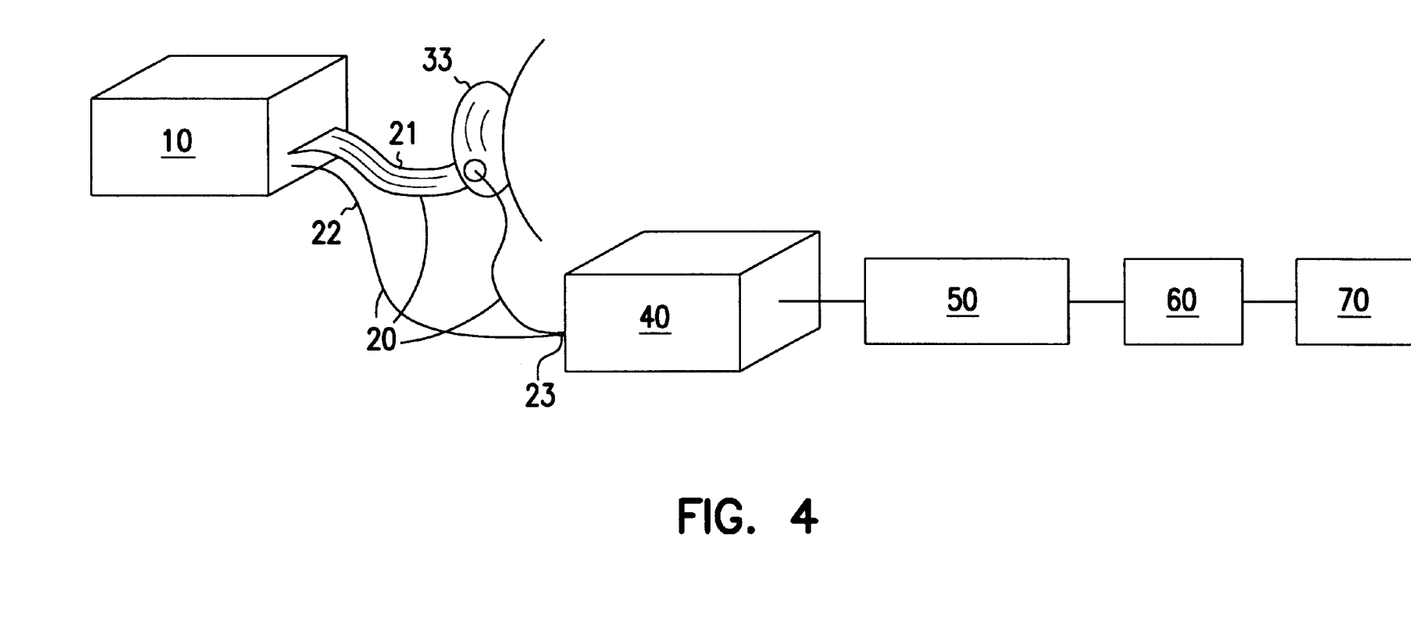
FIG. 4 is a schematic diagram of a second embodiment of the invention, particularly adapted for the non-invasive in-vivo measurement of glycated proteins and lipids by diffuse transmission.

Preferably, the sensor 40 is a parallel-channel diode-array grating spectrometer covering selected regions within the visible and near-infrared portions of the electromagnetic spectrum such as is described in U.S. Pat. No. 4,997,281 granted to the inventor in this application. FIG. 3 shows the optical schematic of this sensor comprising the entrance slit 41, the concave holographic grating 42, a dichroic beamsplitter 43, field-flattening lenses 44, order-sorting filters 45, diode-array detectors 46, and electronics 47 comprising parallel-channel preamplifiers, multiplexers and an analog to digital converter. The outputs of the sensor are then processed by a digital signal processor (DSP) 48 to demultiplex the sample, reference, and dark signals and form the data signals representative of the sample and reference energy in each measured wavelength band corrected for any offsets using the present or previously measured dark signals. Further description of this sensor is incorporated herein by reference to U.S. Pat. No. 4,997,281 issued to the present inventor. FIG. 4 shows the same measurement technology applied to in-vivo measurements by diffuse transmission through a body part 33. Although an earlobe is illustrated, the finger, the web of flesh between the thumb and first finger, or similar sites offering convenient access for the probes may be used.

Figure 5:
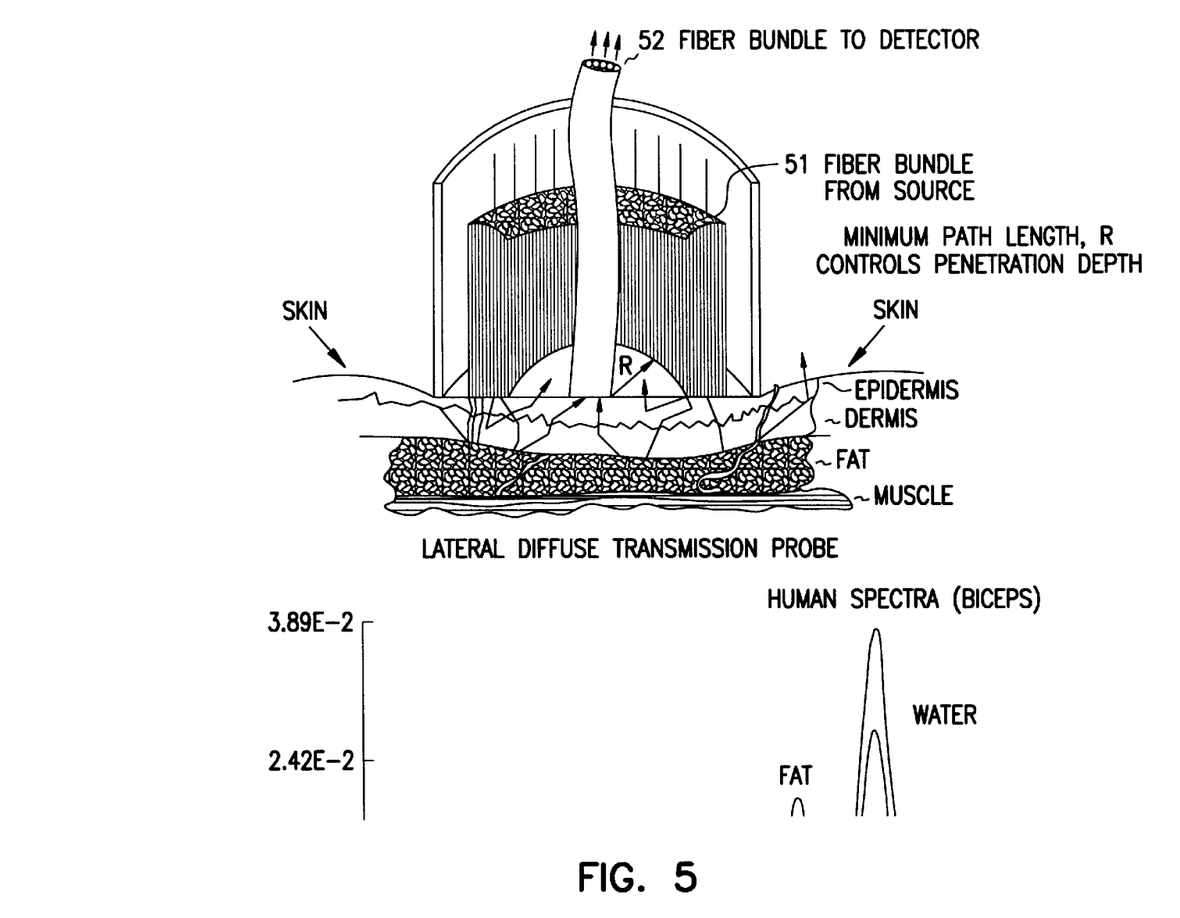
FIG. 5 is a schematic of the geometry of the lateral diffuse transmission or "interactance" measurement using a fiber-optic probe.
Figure 6:
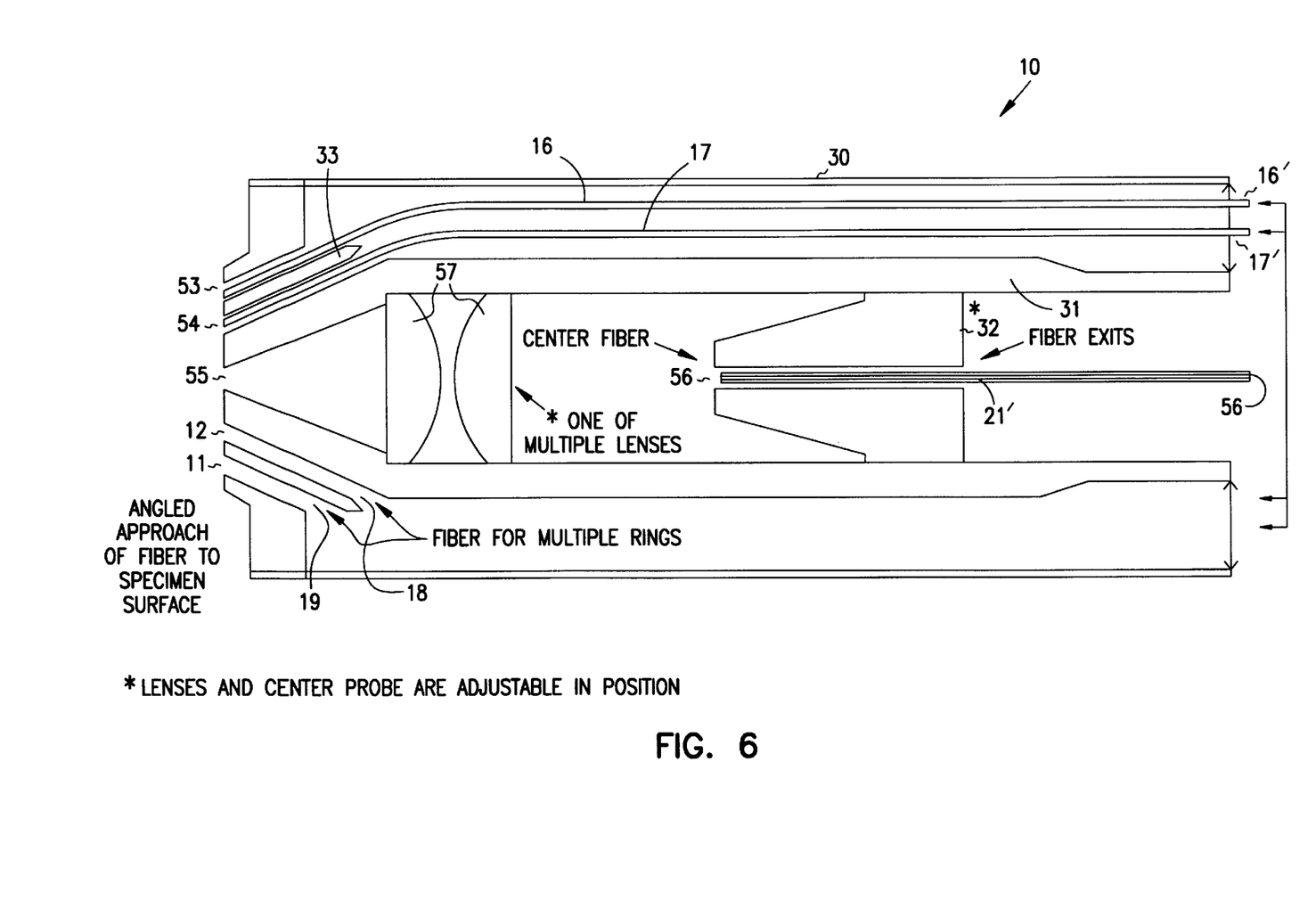
FIG. 6 is a schematic diagram of an improved fiber-optic probe providing two different optical paths within the total measurement volume and measurement from a single surface of the body; and, FIG. 7 is a flow diagram of the steps comprising the methods of this invention.

Illumination and collection of the optical energy may be from the same surface of the body using the technique based on lateral diffuse transmission beneath the surface of the sample from the source to the collector. This measurement is sometimes called "interactance." FIG. 5 shows the geometry at the sample surface using fiber-optic bundles for transmission of light to and from the measurement volume. The source-sample fiber 51 is formed in a ring surrounding the sample-sensor fiber 52 so that the separation between them is constant. The minimum path through the sample is equal to this separation and the mean path is somewhat longer. The depth of penetration of the optical energy is also related to this separation. FIG. 6 shows a schematic cross-section view of an improved probe for optical interactance and transmittance measurements. This probe provides two illuminating rings 53 and 54 surrounding the central collection aperture 55. The sample-sensor fiber-optic bundle 56 may be recessed and imaged on the sample by lenses 57 as shown, or preferably, the lenses may be omitted and the end of the sample-sensor fiber-optic bundle moved into contact with the sample surface. The use of two illuminating rings provides two paths within the sample, allowing the measurement using energy from one ring to form the reference signals and the measurement using energy from the second ring to form the sample signals. The source optical modulator provides multiplexed optical energy to the two illuminating rings. The central sample-sensor bundle 56 is used for energy from both rings, therefore, it is throughput matched to utilize the entire sensor optical throughput. This probe and its use are more fully described in U.S. application Ser. No. 663,144 filed Mar. 1, 1991 by the present inventor which is incorporated herein by reference.

It will be appreciated that other apparatus such as those described in U.S. Pat. No. 4,975,581 issued to Robinson et al. and U.S. Pat. No. 5,077,476 issued to Rosenthal may be used to make in-vitro and in-vivo spectral measurements. The tungsten-halogen source, diode-array sensor and probes described above are most capable of making full spectral measurements sufficiently often to sample the pulse waveform at all wavelengths more frequently than the Nyquist sampling rate required to preserve the temporal information at every wavelength while maintaining the high detectivity required to measure with high signal-to-noise ratio the small energy levels arising after adequate penetration into the body for interaction with the blood. Use of a silicon photovoltaic diode array for detection of wavelengths below a cutoff between 900 and 1100 nanometers and a photovoltaic InGaAs diode array for detection of wavelengths starting from 900 to 1100 nanometers and extending to 1700 nanometers together with parallel channel preamplifiers and anti-aliasing filters before the multiplexer provides a unique combination of speed and sensitivity throughout the useful range of wavelengths for measurement over reasonable sample path lengths.

Figure 7:
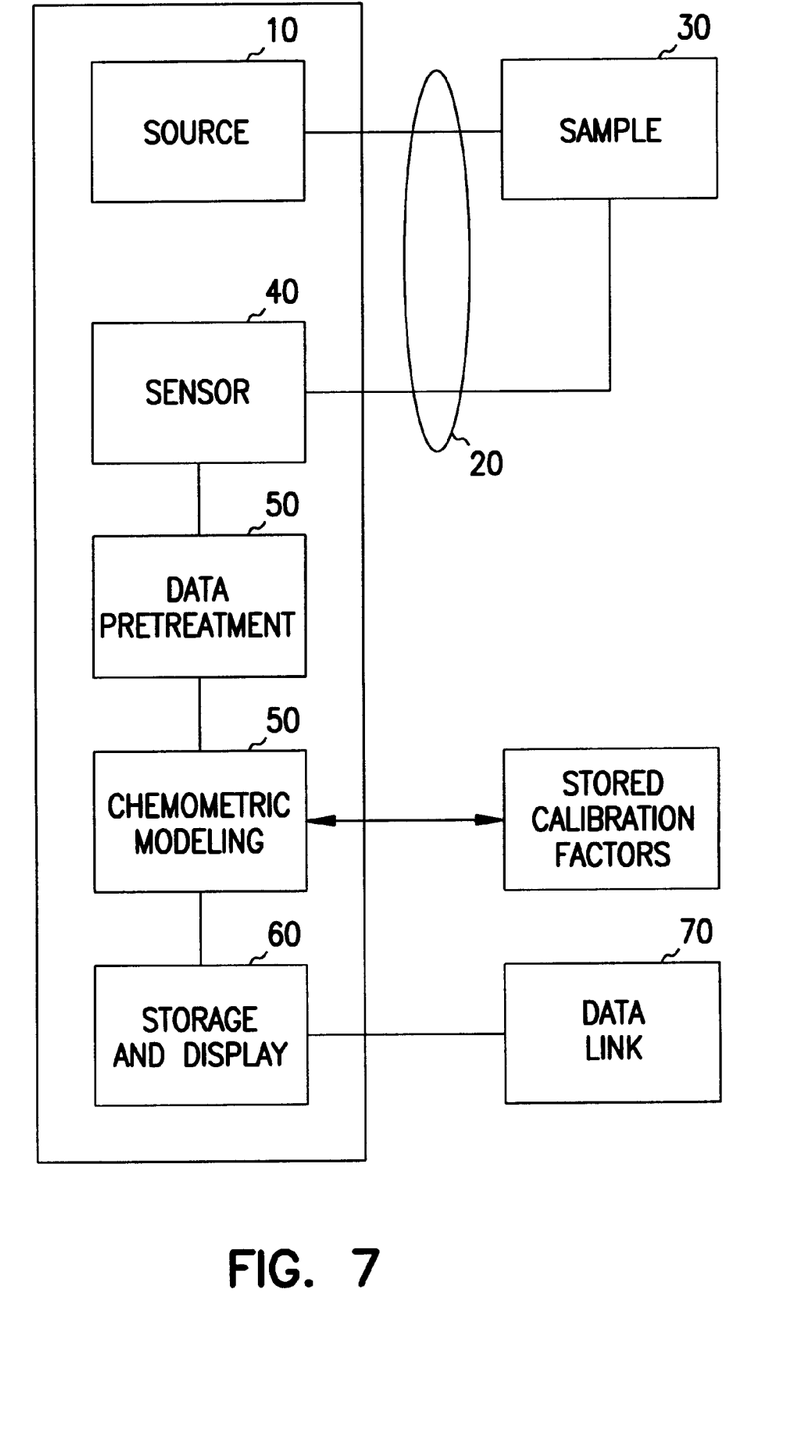

The steps of the method and signal flow of the present invention are shown in block diagram form in FIG. 7. The source 10, energy directing means 51, and sensor 40 have been described above. The data pretreatment comprises one or more corrections to the data signal applied as follows: a) linear transformation to standardize the instrument response function, e.g., wavelength scale adjustment and stray light and optical/electronic cross-talk correction, b) non-linear transformations to approximately linearize the relationship between the amplitude of such standardized data signals, S, and the values of the analytes, e.g., logarithmic, the Kubelka-Munk function, or power series transformations using a summation of terms in powers of S multiplied by predetermined coefficients, and c) additional linear transformations to normalize the linearized data signals, e.g., to reduce the baseline offset and multiplicative effects of the measured geometry and scattering within the sample.

Wavelength scale adjustment is performed by interpolation of new data signal values which are located at standard, equally spaced wavelengths between the measured wavelength band centers by curve fitting, for example, using a local spline function based on the four data signals closest to the standard wavelength. The wavelength correction operator, W, can be expressed as a sparse n×n matrix having values close to the diagonal and zeros elsewhere, where n is the number of measured data points. The interpolation coefficients are determined from measurements of the wavelength response of the instrument and then stored for use in standardization of subsequent data signals. If the original data signals, S, are expressed as a vector of length W, the wavelength standardized data signals, S', are expressed by matrix multiplication as S'=S W.

Stray light and optical/electronic crosstalk correction is performed by measuring all the data signals when energy within a single wavelength band is supplied to the sensor and repeating this measurement for all the wavelength bands. This procedure generates response factors which may be expressed as an n×n response matrix, R, where the data signals $S_R=I_R R$ and the vector $I_R$ of length n expresses the optical intensity input. Therefore data signals S' can be more accurately related to I by $S'=SR^{-1}$ where $RW^{-1}$ is the universe of the matrix of measured R and vector S expresses the measured data signal The diode array spectrophotometer spectral response matrix [R] is determined by measurements using a monochromatic energy source, the wavelength of which can be varied across the entire spectral response of the diode array. This source should have a spectral width much less than the spectral passband of the diode array spectrophotomer and spectral stray light that is less than the desired accuracy of correction. A tunable laser or high quality double monochromator such as the Cary 14, are suitable sources. The entire diode array spectrum is recorded for each wavelength setting of the monochromatic source.

The diode array signal for the jth pixel, $S_j$, after correction for offsets (determined by dark measurement with no input energy), can be described as follows:

$$S_j = I_j R_{jj} T_{jj} + \Sigma_i (I_i R_{ij} C_{ij})$$

where $I_j$ is the input energy at wavelength j, i.e., at wavelengths within the passband of pixel j, $R_{jj}$ is the signal response of pixel j to energy at wavelength j, $T_{jj}$ is the energy transmission efficiency for wavelength j from the input slit to the pixel j (including the effect of energy lost to other pixels as spectral stray light), $I_i$ is the input energy at wavelength i outside the spectral passband of pixel j, $R_{ij}$ is the response of pixel j to energy at wavelength i, and $C_{ij}$ is the stray light coupling of energy at wavelength i to pixel j. The sum over i describes the total spectral stray light at pixel j.

In matrix form, the signal spectrum can be written: [S]=[1]×[R'] where $$[R'] = \begin{vmatrix} R_{11}T_{11} & R_{12}C_{12} & \ldots & R_{ij}C_{ij} \\ R_{21}C_{21} & R_{22}T_{22} & \ldots & R_{2j}C_{2j} \\ \ldots & \ldots & \ldots & \ldots \\ R_{i1}C_{i1} & R_{i2}C_{i2} & \ldots & R_{jj}T_{jj} \end{vmatrix}$$

Using a monochromatic source of known intensity, each member of the response matrix can be individually determined. These terms are a function of the optical geometry of the diode array spectrophotometer only, and are therefore constant so long as that geometry is not changed.

The correction can now be made as:

[I]=[S]×[R']$^{-1}$, where I equals the stray corrected signal, S'.

The preferred linerization is based on first computing the negative log of the ratio of the sample and reference data signal values to form new "absorbance" data signals, A, representative of the combination of the component absorptions and the scattering effects within the sample with the source intensity factor removed. The logarithm has the property that multiplicative factors in the argument are converted to a summation of terms and exponential terms are converted to multiplicative factors.

A preferred normalization to correct such baseline offset and multiplicative effects is the improved multiplicative scatter correction which is the subject of U.S. Pat. application Ser. No. 572,534, filed on Aug. 28, 1990, by the present inventor and co-inventor Harald Martens which is incorporated herein by reference. Unlike the derivative and derivative ratio methods described by Rosenthal, or two wavelength normalization techniques, the above technique utilizes substantially all of the linearized data signals and a stored target set of linearized data signal values to determine the correction coefficients for offset and slope.

The extraction of the temporal waveforms of the signals related to components in the blood is preferably performed by forming the weighted sum of normalized data signals at different wavelengths to optimally define a blood data signal. This signal is largely derived from the total hemoglobin absorption as hemoglobin is a strong absorber, particularly below 900 nm, specifically associated with the red blood cells. Chemometric modelling in the absorbance wavelength domain is useful to define the weights applied to the data signals to optimize separation of the blood data signal from interference of other tissue signals. The blood temporal reference signal is obtained by digital filtering of the blood data signal to extract the pulse waveform from the other temporal variations caused by motion of the body or other extraneous factors. The blood temporal reference signal is then used as the reference for correlation in the time domain with each of the linearized data signals to produce modified data signals representative of the portion of the linearized data signals derived from components within the blood separated from the portion derived from other tissues within the body. This technique provides the ability to separate the blood portion of data signals, even in wavelength bands for which the relative magnitude and spectral overlap of the absorptions of multiple components of the blood and other tissues make determination of the blood component otherwise difficult or impossible. For example, data signals from the wavelength bands below 900 nm may be used to separate blood related signals from wavelength bands up to 1700 nm, although the longer wavelength data signals are spectrally similar to and weaker than the interfering data signals from other tissues.

The chemometric models preferably use the normalized data signals of all or at least a large portion of the measured wavelength bands, although optimization of the wavelength bands utilized is contemplated by this invention. Therefore, modeling techniques such as partial least squares regression (PLS) and principal component regression (PCR), well known to the art, (see "Multivariate Calibration", Martens and Naes, Wiley, 1989) are preferred. Unlike Robinson, et al. (U.S. Pat. No. 4,975,581), the models are constructed using a calibration sample set containing more samples than the number of wavelength bands included in the calibration. The classification of measured data signals, as discussed by Martens and others, and subsequent choice of the chemometric model to apply, provides the means to further optimize the determination of analyte values. Calculation of the spectral residue resulting from the chemometric modelling provides a basis for confirming the reliability of the analysis, and, therefore, a second means for selecting the optimum among several chemometric models.

It will be appreciated by those skilled in the art that various linear operations may be combined into a single operator and that the order in which linear operations are preformed may be changed using the known techniques of matrix algebra.

The signal pretreatment and chemometric modeling is preferably performed by a floating point digital signal processor using a semiconductor device such as the Analog Devices ADSP 21020, although a general purpose computer using a device such as the Intel 80486 can also perform such operations.

The analyte values together with time and data information are stored in digital semiconductor memory and recalled for display as desired by the user. In order to transfer the present or previously stored analyte values, time and date to external devices, a digital data link is provided. Preferably this is an optical link transmitting directly through the air to an external computer or data station, although radio or a wire connection may be used. If the data is to be transmitted continuously, e.g., for monitoring or control of an insulin pump, optical transmission via fiber optics is preferred to avoid electromagnetic interference from external sources.

In addition to determining the amounts of glycated compounds in blood, the method and apparatus of the present invention may be employed for the direct measurement of glucose. The direct measurement of glucose is preferably performed using energy having a wavelength between 1110 to 1560 nm.

In addition, the present invention may use pulse waveforms having wavelengths in the visible and NIR ranges. The pulse waveforms may be used for the measurement of glycated compounds, as well as for the direct measurement of glucose.

The pulse waveforms, when used for the direct measurement of glucose in the 1110 to 1560 nm range may be derived from a waveform having a wavelength below 1110 nm. This allows separation of the signals.

Furthermore, the present invention may be employed to measure labile hemoglobin compounds in the visible wavelength range using an increased number of wavelengths and chemometric modelling techniques. Preferably, the wavelengths range from 520 to 620 nm.

While preferred embodiments of the present invention have been shown and described it will be understood by those skilled in the art that various changes and modifications could be made without varying from the scope of the present invention.

What is claimed is:

1. In apparatus for determining the response to electromagnetic energy received after passing through material in a measurement volume using a calibrated diode array spectrometer to modify electrical signals developed from said response, the improvement comprising means for calibrating the response of the diode-array spectrometer including:

a) means for measuring the spectral response of each diode-array signal channel over a substantial part of wavelength range covered by said diode-array spectrometer by introducing to said diode-array spectrometer electromagnetic radiation
      1) for which the characteristics over said substantial part of wavelength range are known to higher spectral resolution than the spectral width of each diode-array element and
      2) for which higher energy amplitude accuracy is known than the desired energy amplitude accuracy of the diode-array spectrometer, and recording electrical data signal outputs for each diode-array channel as a function of the wavelength of said introduced electromagnetic energy over said substantial part of wavelength range covered by said diode-array spectrometer;

b) means for calculating response factors of each of said diode-array signal channels as the ratio of said electrical data signal output, S, to the output electromagnetic energy for its associated wavelength band ($R_{jj}T_{jj}$) and for each of the other wavelength bands associated with the other diode-array signal channels ($R_{ij}C_{ij}$) where $T_{jj}$ represents the transmission efficiency for energy in wavelength band j to diode-array element j and $C_{ij}$ is the coupling of energy in wavelength band I to the diode-array element j, which response factors may be expressed as an n by n response matrix; and c) means for forming corrected data signals, S', in accordance with the matrix multiplication $[S] \times [R]^{-1}$ where $[R]^{-1}$ is the inverse of said measured and calculated matrix [R].

2. The apparatus of claim 1 wherein electromagnetic radiation between the wavelength range of 380 nm and 2500 nm has been introduced into the diode-array spectrometer.

3. The apparatus of claim 1 wherein electromagnetic radiation introduced into the spectrometer is monochromatic.

4. The apparatus of claim 1 wherein electromagnetic radiation introduced into the diode-array spectrometer is produced using a monochromator.

5. The apparatus of claim 1, wherein electromagnetic radiation introduced into the diode-array spectrometer is produced using a tunable laser.

6. In a method for determining the response to electromagnetic energy received after passing through material in a measurement volume using a calibrated diode array spectrometer to modify electrical signals developed from said response, the improvement comprising:

calibrating the response of the diode-array spectrometer by:

a) measuring the spectral response of each diode-array signal channel over a substantial part of wavelength range covered by said diode-array spectrometer by introducing to said diode-array spectrometer electromagnetic radiation
  1) for which the characteristics over said substantial part of wavelength range are known to higher spectral resolution than the spectral width of each diode-array element and
  2) for which higher energy amplitude accuracy is known than the desired energy amplitude accuracy of the diode-array spectrometer, and recording electrical data signal outputs for each diode-array channel as a function of the wavelength of said introduced electromagnetic energy over said substantial part of wavelength range covered by said diode-array spectrometer;

b) calculating response factors of each of said diode-array signal channels as the ratio of said electrical data signal output, S, to the output electromagnetic energy for its associated wavelength band ($R_{jj}T_{jj}$) and for each of the other wavelength bands associated with the other diode-array signal channels ($R_{ij}C_{ij}$) where $T_{jj}$ represents the transmission efficiency for energy in wavelength band j to diode-array element j and $C_{ij}$ is the coupling of energy in wavelength band I to the diode-array element j, which response factors may be expressed as an n by n response matrix; and c) forming corrected data signals, S', in accordance with the matrix multiplication $[S] \times [R]^{-1}$ where $[R]^{-1}$ is the inverse of said measured and calculated matrix [R].

7. The method of claim 6, including the additional step of using said method for correction of optical stray energy and electrical crosstalk.

8. Apparatus for determining the response to electromagnetic energy received after passing through material in a measurement volume using a calibrated diode array spectrometer, the apparatus comprising means for calibrating the response of the diode-array spectrometer including:
  a) means for measuring the spectral response of each diode-array signal channel over a substantial part of wavelength range covered by said diode-array spectrometer by introducing to said diode-array spectrometer electromagnetic radiation
    1) for which the characteristics over said substantial part of wavelength range are known to higher spectral resolution than the spectral width of each diode-array element and
    2) for which higher energy amplitude accuracy is known than the desired energy amplitude accuracy of the diode-array spectrometer, and recording electrical data signal outputs for each diode-array channel as a function of the wavelength of said introduced electromagnetic energy over said substantial part of wavelength range covered by said diode-array spectrometer;

b) means for calculating response factors of each of said diode-array signal channels as the ratio of said electrical data signal output, $S_j$, to the input electromagnetic energy for its associated wavelength band ($R_{jj}T_{jj}$) and for each of the other wavelength bands associated with the other diode-array signal channels ($R_{ij}C_{ij}$) where $T_{jj}$ represents the transmission efficiency for energy in wavelength band j to diode-array element j and $C_{ij}$ is the coupling of energy in wavelength band I to the diode-array element j, which response factors may be expressed as an n by n response matrix; and c) means for forming corrected data signals, S', in accordance with the matrix multiplication $[S] \times [R]^{-1}$ where $[R]^{-1}$ is the inverse of said measured and calculated matrix [R] and vector [S] expresses a measured data signal.

9. A method for determining the response to electromagnetic energy received after passing through material in a measurement volume using a calibrated diode array spectrometer, the method comprising:

calibrating and correcting the response of the diode-array spectrometer by:
  a) measuring the spectral response of each diode-array signal channel over a substantial part of wavelength range covered by said diode-array spectrometer by introducing to said diode-array spectrometer electromagnetic radiation
    1) for which the characteristics over said substantial part of wavelength range are known to higher spectral resolution than the spectral width of each diode-array element and
    2) for which higher energy amplitude accuracy is known than the desired energy amplitude accuracy of the diode-array spectrometer, and recording electrical data signal outputs, $S_j$, for each diode-array channel as a function of the wavelength of said introduced electromagnetic energy over said substantial part of wavelength range covered by said diode-array spectrometer;

b) calculating response factors of each of said diode-array signal channels as the ratio of said electrical data signal output, $S_j$, to the input electromagnetic energy for its associated wavelength band ($R_{jj}T_{jj}$) and for each of the other wavelength bands associated with the other diode-array signal channels ($R_{ij}C_{ij}$) where $T_{jj}$ represents the transmission efficiency for energy in wavelength band j to diode-array element j and $C_{ij}$ is the coupling of energy in wavelength band I to the diode-array element j, which response factors may be expressed as an n by n response matrix; and c) forming corrected data signals, S', in accordance with the matrix multiplication $[S] \times [R]^{-1}$ where $[R]^{-1}$ is the inverse of said measured and calculated matrix [R] and vector [S] expresses measured data signals.

10. The method of claim 9 wherein electromagnetic radiation between the wavelength range of 380 nm and 2500 nm has been introduced into the diode-array spectrometer.

11. The method of claim 9 wherein electromagnetic radiation introduced into the spectrometer is monochromatic.

12. The method of claim 9 wherein electromagnetic radiation introduced into the diode-array spectrometer is produced using a monochromator.

13. The method of claim 9 wherein electromagnetic radiation introduced into the diode-array spectrometer is produced using a tunable laser.

* * * * *